United States Patent [19]

Kaplan

[11] 4,415,747
[45] Nov. 15, 1983

[54] PROCESS FOR MAKING ETHYLENE GLYCOL DERIVATIVES

[75] Inventor: Leonard Kaplan, Dunbar, W. Va.

[73] Assignee: Union Carbide Corporation, Danbury, Conn.

[21] Appl. No.: 307,074

[22] Filed: Sep. 29, 1981

[51] Int. Cl.$^3$ .............................................. C07C 69/76
[52] U.S. Cl. ..................................... 560/112; 560/224; 560/263; 260/410.6; 556/443; 568/672; 568/858; 568/877
[58] Field of Search ...................... 560/263, 112, 224; 556/443; 260/410.6; 568/672, 858, 877

[56] References Cited

U.S. PATENT DOCUMENTS 3,053,883  9/1962  Dean et al. ........................... 560/112

FOREIGN PATENT DOCUMENTS 871767  6/1961  United Kingdom ................ 560/112

Primary Examiner—Paul J. Killos
Attorney, Agent, or Firm—Norman L. Balmer

[57] ABSTRACT

This process is concerned with the reductive coupling of α-halo ethers and/or α-halo esters to make ethylene glycol derivatives by carrying out the reductive coupling process in the presence of an iron compound having iron in an oxidation state of zero.

18 Claims, No Drawings

PROCESS FOR MAKING ETHYLENE GLYCOL DERIVATIVES

The instant process is directed to the production of ethylene glycol derivatives by the reductive coupling of α-halo ethers or α-halo esters in the presence of an iron compound having iron in the zero oxidation state. These derivatives of ethylene glycol may be subsequently hydrolyzed to give ethylene glycol.

Ethylene glycol is commercially produced by the hydrolysis of ethylene oxide which in turn is generated by the oxidation of ethylene, typically by the reaction of ethylene and oxygen over a silver containing catalyst. The reaction is a heterogeneous gas phase reaction. Other processes (non-commercial) for making glycol involve reactions of carbon monoxide with hydrogen or formaldehyde, typically in the presence of a precious metal catalyst. Such processes are described as being operated at pressures as low as 1 atmosphere to 3400 atmospheres. The future anticipated shortages of petroleum based starting materials was prompted significant interest in such alternative routes to ethylene glycol using a source other than a petroleum source. Such an alternative source is formaldehyde which may be produced from methanol which may be produced from synthesis gas, i.e., a mixture of oxides of carbon and hydrogen.

The instant process provides for the formation of ethylene glycol derivatives by the reductive coupling of α-halo ethers or α-halo esters which may be formed from formaldehyde and the corresponding alcohol or carboxylic acid, in the presence of an acid HX where X is Cl, Br or I.

The reaction of iron pentacarbonyl with gem-dihalides is reported in C. E. Coffey, "Reaction of Iron Pentacarbonyl with gem-dihalides," J.Am. Chem Soc., 83, 1623 (1961). The authors therein report the reaction of gem-dihalide to form a carbon-carbon bond at the respective carbons which had the halogen atoms. The resultant products may be saturated or unsaturated and provide no basis for making ethylene glycol or derivatives thereof.

The reaction of α-halo ketones in the presence of iron pentacarbonyl is reported in H. Alper and E. C. H. Keung, "The Formation of 1,4 Diketones, Monoketones, and β-Epoxy Ketones by Reaction of Iron Pentacarbonyl with α-Halo Ketones. A Possible Mechanism for Iron Pentacarbonyl-Halide Reactions," J. Org. Chem., 37 2566 (1972). The authors discuss the reaction of α-halo ketones to form 1,4 diketones, monoketones and β-Epoxy Ketones. The reported products have no utility in the production of ethylene glycol or derivatives thereof.*

*See: Tien-Yau Luh et al., "Iron Pentacarbonyl Promoted Reductive Debromination of α-Bromo Ketones," J. Org. Chem., 44, 641 (1979) wherein the authors report that with the use of slightly higher concentration of iron pentacarbonyl (two fold excess of iron pentacarbonyl) α-bromo ketones can smoothly be reduced to the corresponding ketones, instead.

The instant process, as compared to the above-discussed publications, provides a process that can lead to valuable products such as ethylene glycol or derivatives thereof.

SUMMARY OF THE INVENTION

The instant process provides the formation of ethylene glycol derivatives having the general formula

from α-halo ethers and/or α-halo esters having a general formula:

Y-O-CH$_2$-X wherein Y represents the substituent R- or

wherein R is a monovalent hydrocarbon radical, or Y is

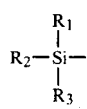

wherein R$_1$, R$_2$ and R$_3$ are monovalent hydrocarbon radicals although R$_1$, R$_2$ and R$_3$ need not be the same; X is at least one of Cl, Br or I. The process is carried out in the presence of an iron compound having iron in the zero oxidation state at a temperature and pressure sufficient to form said ethylene glycol derivatives.

DETAILED DESCRIPTION OF THE INVENTION

The process of this invention relates to a process for the reductive coupling of α-halo ethers or α-halo esters to give ethylene glycol derivatives. These ethylene glycol derivatives may be further reacted to give ethylene glycol, if desired.

The α-halo ethers and α-halo esters employed in the process of the invention are of the general formula

Y-O-CH$_2$X wherein Y is R- or

and X is at least one of Cl, Br or I. The substituent R is a monovalent hydrocarbon radical including alkyl, aryl, aralkyl, alkylaryl, alkenyl and alkynyl; Y can contain alcohol, ester, nitrile, keto groups, and the like. In addition, R- may be substituted with a moiety that does not interfere with the process. In general the substituent R preferably contains from 1 to about 30 carbon atoms and more preferably contains from 1 to about 6 carbon atoms. The substituent Y may also be

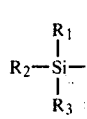

wherein R$_1$, R$_2$, and R$_3$ may be what R may be and may be the same or different monovalent hydrocarbon radicals.

The ethylene glycol derivatives formed herein are of the general formula:

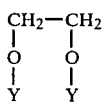

where Y is as previously defined. In addition, a halogen containing iron compound is formed as a product of the process and contains iron in an oxidation state other than zero which may be subsequently treated to regenerate iron in the zero oxidation state for use in this process.

The iron catalyst employed in the process of this invention may be elemental iron or any iron-containing compound having iron in the zero oxidation state, such as iron carbonyls, e.g., $Fe_2(CO)_9$, $Fe_3(CO)_{12}$ and $Fe(CO)_5$.

The process of this invention can be carried out in a homogeneous or heterogeneous reaction mixture. The reactants can be in the vapor or liquid phase. In preferred embodiments, iron carbonyl compounds as defined herein which are soluble in the reaction medium give outstanding results. However, the synthesis of the ethylene glycol derivatives can be suitably effected by using iron compounds which are not homogeneously distributed throughout the reaction mixture. Solid iron compounds which remain in place during the course of the reaction may also be employed. Suspensions of liquid or solid iron compounds in liquid and/or gaseous media, e.g., solvent may be employed. In suitable embodiments of the invention the iron compound can be used in combination with inert materials or contained or deposited on porous supports such as alumina, silica-alumina, silica gel, activated charcoal, titania, zirconia, zeolites as well as the zeolitic molecular sieves, pumice, kieselguhr, inert porous organic polymers (e.g., reticulated cation exchange resin) and the like.

Solvents suitable in the practice of this invention are any materials which are liquid under the reaction conditions, which dissolve the α-halo ester or α-halo ester, and are essentially inert to the reaction. A solvent is essentially inert to the reaction when it does not prevent the reaction from occurring. This does not mean that the solvent is incapable of entering into a reaction concurrently with the reaction of choice. However, it is impractical to use solvents that so severely compete for one or more of the reactants as to adversely affect the economic viability of this process. This is not the case when one of the reactants is a solvent in the reaction.

Illustrative of suitable solvents are, e.g., ketones such as acetone, methyl ethyl ketone, dibutyl ketone, acetophenone, diphenyl ketone and acetylacetone; hydrocarbons such as benzene, hexane, undecane, naphthalene, t-butyl benzene, tetralin, decalin, and the like; ethers such as dimethyl ether, diethyl ether, di-n-butyl ether, diphenyl ether, and the like; sulfones and sulfoxides such as dimethyl sulfoxide and sulfolane; alcohols such as methanol, ethanol, stearyl alcohol, cyclohexanol, and the like; esters such as ethyl acetate, isopropyl acetate, methyl propionate, n-butyl acetate, and the like; amides such as N,N-dimethyl formamide, N,N-diethylacetamide, and the like; lactones such as butyrolactone, caprolactone, and the like; nitriles such as acetonitrile, butyronitrile, and the like.

The reaction may be carried out at extremely low to extremely high temperatures. The minimum temperature is that at which the reaction will proceed sufficient to form the ethylene glycol derivatives. The maximum temperature is that at which one or more of the reactants or solvents combust, detonate or severely decompose (prematurely). The temperatures at which the reaction can be carried out range between about 50° C. and about 400° C. or higher, preferably between about 50° C. and about 300° C.

The pressures at which the reaction can be effected are not narrowly critical and are those pressures sufficient to form the ethylene glycol derivatives. The reaction can be carried out under subatmospheric to superatmospheric pressures. If the solvent is non-volatile under subatmospheric pressures, the pressure employed can be as low as 1 micron of mercury, or lower. The maximum pressure is based upon the pressure needs imposed by the reactants used and the other conditions of the reaction. For example, pressures as high as 50 atmospheres or greater can be employed; for example a gas-phase process running at such pressures over a heterogeneous catalyst can be envisioned.

The concentration of the iron catalyst employed in the instant process will depend in part on the nature of the α-halo ether or α-halo ester employed, and the final oxidation state at which iron exits at the end of the reaction. The amount of the iron compound employed is the amount necessary to provide for the formation of the ethylene glycol derivative product with greater amounts being employed to provide for the formation of product as desired. The amount of iron catalyst employed is generally between about 1 mole percent (based upon the moles of α-halo ether and/or α-halo ester employed) and about a 3 fold molar excess (based upon moles of α-halo ether and/or α-halo ester employed).

The time needed to carry out the process can be as low as fractions of a second to hours, even to days. Heterogeneous vapor phase reactions may be run in less than a second, and some homogeneous liquid phase reactions require hours before the process is completed. Generally, the time required for carrying out the process is between about 0.01 second and about 50 hours and preferably between about 0.1 second and 20 hours.

The novel process can be executed in a batch, semicontinuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) if desired. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well known to the art. The iron compound may be initially introduced into the reaction zone batchwise, or it may be continuously or intermittently introduced into such zone during the course of the synthesis reaction. Means to introduce and/or adjust the reactants (α-halo ethers or α-halo esters) either intermittently or continuously into the reaction zone during the course of the reaction can be conveniently utilized in the novel process especially to maintain the desired molar ratios of and the partial pressures exerted by the reactants.

The ethylene glycol derivatives prepared by the instant process may be further reacted to provide ethylene glycol as the product. When ethylene glycol is the desired product the ethylene glycol derivatives formed herein may be hydrolyzed to give ethylene glycol. The hydrolysis of ethylene glycol derivatives is well known in the art. The preferred ethylene glycol derivatives for use in forming ethylene glycol are those derivatives wherein

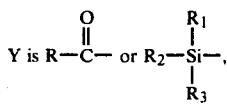

as hereinbefore described and most preferably a haloalkyl benzoate (e.g. chloromethyl benzoate).

The process is preferably carried out in a continuous or cyclic mode with regeneration of the halogen acid HX (X is at least one of Cl, Br and I) and the iron catalyst from the halogen-containing iron compound, wherein said regeneration may be effected by contacting the halogen-containing iron compound with hydrogen. If an iron carbonyl is desired as the iron catalyst, the halogen-containing iron compound may be contacted with hydrogen and carbon monoxide. This mixture may then be reacted with the product of the reaction of alcohol or carboxylic acid with formaldehyde.

The following examples are merely illustrative of the invention and are not presented as a definition of the limits of the invention:

EXAMPLE 1

In accordance with the invention a solution of 61 milligram (0.36 millimole) of chloromethyl benzoate (i.e. wherein Y is phenyl and X is Cl), bp 80°/3 mm, was mixed with 83 milligrams (0.42 millimole) of iron pentacarbonyl, bp 78°, in 0.5 milliliter (0.67 gram) of sulfolane [purified sequentially according to the procedure in G. Choux and R. L. Benoit, J.Am. Chem Soc., 91, 6221 (1969) and E. N. Arnett and C. F. Douty, J.Am. Chem. Soc., 86, 409 (1964)], bp 105°–7°/3 mm. The mixture was placed in a glass NMR (Nuclear Magnetic Resonance) tube (4 millimeter (ID)×7 inches) and heated under vacuum at 140° C. for about 3 hours. The mixture was analyzed by vapor phase chromatography (6 foot×¼ inch (OD) column using Chromosorb 101 (TM); Helium flow rate of 67 milliliter/min; injection port temperature of 270° C.; initial column temperature of 150° C. with heating at 4° C./min for 18 minutes then at 20° C./min to 275° C.; thermal conductivity detector maintained at 300° C.; retention time 36–38 minutes) and by mass spectroscopy which indicated the formation of ethylene glycol dibenzoate. A yield of 12 mole percent (0.021 millimole) of ethylene glycol dibenzoate was observed, based on moles of chloromethyl benzoate.

The ethylene glycol dibenzoate may be hydrolyzed to form ethylene glycol and the halogen-containing iron compound may be contacted with hydrogen and carbon monoxide to form the halogen acid HCl and an iron carbonyl for reuse in the process.

EXAMPLE 2

This example was carried out according to example 1 except that 0.71 gram of chloromethyl benzoate, 0.87 gram of iron pentacarbonyl, 5 milliliters of sulfolane, a reaction time of 4 hours were employed, and the mixture was placed in a glass ampule (5/8 inch (OD)×4¼″) instead of the glass NMR tube employed in example 1. Analysis by vapor phase chromatography indicated the presence of ethylene glycol dibenzoate. The ethylene glycol dibenzoate and halogen-containing iron compound may be treated as in example 1.

EXAMPLE 3

This example was carried out according to example 1 except that 61 milligrams of chloromethyl benzoate, 94 milligrams of iron pentacarbonyl, and 0.5 milliliter of benzene were employed. Further, the mixture was heated under vacuum at 140° C. for 3 hours and then at 170° C. for an additional 3 hours. Analysis by vapor phase chromatography indicated the presence of ethylene glycol dibenzoate. The ethylene dibenzoate and halogen-containing iron compound may be treated as in example 1.

What is claimed is:

1. The process for making ethylene glycol derivatives of the formula (I):

comprising reacting an α-halo compound of the formula (II):

wherein the substituent Y is R— or

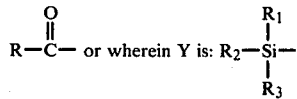

wherein R, $R_1$, $R_2$ and $R_3$ may each be a monovalent hydrocarbon of 1 to about 30 carbon atoms, and X is at least one of Cl, Br and I, by reacting said α-halo compound in the presence of an iron compound having iron in the zero oxidation state at a temperature and pressure sufficient to form such ethylene glycol derivatives.

2. The process of claim 1 wherein the monovalent hydrocarbon is aryl.

3. The process of claim 2 wherein the monovalent hydrocarbon is phenyl.

4. The process of claim 3 wherein Y is a haloalkyl benzoate.

5. The process of claim 1 wherein the process is carried in the presence of a solvent.

6. The process of claim 5 wherein the solvent is benzene.

7. The process of claim 5 wherein the solvent is sulfolane.

8. The process of claim 1 wherein the iron compound is an iron carbonyl.

9. The process for making ethylene glycol which comprises the following steps:

(a) preparing an α-halo compound (I) having the formula:

-continued by the reaction of Y—OH, formaldehyde and an acid HX;

wherein Y is 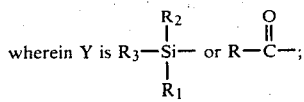

wherein R, $R_1$, $R_2$ and $R_3$ are each monovalent hydrocarbon substituents of one to about 30 carbon atoms and X is at least one of Cl, Br or I;

(b) reacting (I) in the presence of an iron catalyst having iron in the zero oxidation state at a temperature and pressure sufficient to form an ethylene glycol derivative (II) of the formula:

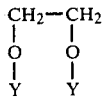 (II)

and a halogen-containing iron compound wherein iron is in an oxidation state other than zero; and (c) hydrolyzing (II) to give ethylene glycol and Y—OH.

10. The process of claim 9 wherein Y—OH of step (c) is recycled to step (a).

11. The process of claim 10 wherein the process is a continuous process.

12. The process of claim 9 having the further step (d) wherein the halogen-containing iron compound of step (b) containing halogen X and iron is reacted with hydrogen to provide HX and an iron product wherein at least a portion of the iron is in the zero oxidation state.

13. The process of claim 12 having the further step:
(e) recycle the HX of step (d) to step (a) and the iron product step (d) to step (b).

14. The process of claim 13 wherein prior to step (e) the iron is contacted with carbon monoxide to provide an iron carbonyl.

15. The process of claim 9 wherein the formaldehyde is produced from methanol.

16. The process of claim 15 wherein the methanol is produced from a mixture of oxides of carbon and hydrogen.

17. The process of claim 1 wherein the time required for carrying out the process is between about 0.01 second and about 50 hours.

18. The process of claim 17 wherein the time required for carrying out the process is between about 0.1 second and about 20 hours.

* * * * *